(12) United States Patent
Wang

(10) Patent No.: US 9,038,435 B2
(45) Date of Patent: May 26, 2015

(54) MEASUREMENT OF CARBON TO HYDROGEN RATIO IN HYDROCARBONS

(71) Applicant: ExxonMobil Research and Engiineering Company, Annandale, NJ (US)

(72) Inventor: Frank C Wang, Annandale, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 254 days.

(21) Appl. No.: 13/669,813

(22) Filed: Nov. 6, 2012

(65) Prior Publication Data

US 2013/0125619 A1    May 23, 2013

Related U.S. Application Data

(60) Provisional application No. 61/561,170, filed on Nov. 17, 2011.

(51) Int. Cl.
*G01N 30/02* (2006.01)
*G01N 30/74* (2006.01)
*G01N 30/88* (2006.01)

(52) U.S. Cl.
CPC ........ *G01N 30/74* (2013.01); *G01N 2030/8854* (2013.01)

(58) Field of Classification Search
CPC ...................... G01N 30/74; G01N 2030/8854
USPC ......................................................... 73/23.38
See application file for complete search history.

(56) References Cited

U.S. PATENT DOCUMENTS 6,275,775 B1    8/2001    Baco et al.

*Primary Examiner* — Laura Martin
*Assistant Examiner* — Alex Devito
(74) *Attorney, Agent, or Firm* — Glenn T. Barrett; Andrew T. Ward

(57) ABSTRACT

The ratio of carbon to hydrogen in hydrocarbon samples is determined using gas chromatography and atomic emission detection. Comparison of the carbon to hydrogen ratio from different samples allows for qualitative determination of relative hydrogen content. Establishing a carbon to hydrogen ratio for a reference sample allows a further quantitative determination of carbon to hydrogen ratio.

20 Claims, 9 Drawing Sheets

MEASUREMENT OF CARBON TO HYDROGEN RATIO IN HYDROCARBONS

FIELD OF THE INVENTION

This invention provides methods for characterizing ratios of carbon to hydrogen in petroleum and/or biologically derived feedstocks.

BACKGROUND OF THE INVENTION

Petroleum products have application in a variety of uses, including using as lubricants and as feedstock for forming various plastics, polymers, and other chemicals. However, fuel applications are still a dominant use for all types of petroleum streams. In a fuel application, the value of a petroleum product is related to the amount of energy provided per unit weight or volume. Unfortunately, the energy value of a petroleum sample is not immediately apparent from directly observable characteristics of a sample, such as viscosity or specific gravity.

U.S. Pat. No. 6,275,775 describes methods for correlating properties determined by conventional methods with measurements made using a chromatography technique. The described methods start by determining properties for a set of sample compounds using a conventional method, such as using an ASTM method for determining cetane. The reference set of compounds are then characterized using chromatography combined with another spectroscopic technique to characterize the compounds relative to boiling point. The two measurements for the reference compounds are then used to build a model. An unknown sample is then measured using the chromatography and spectroscopic technique, and the model is used to determine the correlated property value for the unknown sample in relation to a predicted boiling point profile for the unknown sample.

SUMMARY OF THE INVENTION

In an embodiment, a method is provided for characterizing the ratio of hydrogen to carbon in a sample. The method includes separating a plurality of compounds in a first hydrocarbon sample using gas chromatography; measuring atomic emissions from carbon atoms and hydrogen atoms for one or more compounds from the first hydrocarbon sample; determining a first hydrogen to carbon peak area ratio based on the hydrogen peak area and carbon peak area for the one or more compounds from the first hydrocarbon sample; separating a plurality of compounds in a second hydrocarbon sample using gas chromatography; measuring atomic emissions from carbon atoms and hydrogen atoms for one or more compounds from the second hydrocarbon sample; determining a second hydrogen to carbon peak area ratio based on the hydrogen peak area and carbon peak area for the one or more compounds from the second hydrocarbon sample; and comparing the first hydrogen to carbon peak area ratio and the second hydrogen to carbon peak area ratio.

In another embodiment, a method is provided for characterizing the ratio of hydrogen to carbon in a sample. The method includes separating a plurality of compounds in a hydrocarbon sample using gas chromatography; measuring atomic emissions from carbon atoms and hydrogen atoms for one or more compounds from the hydrocarbon sample; determining a hydrogen to carbon peak area ratio based on the hydrogen peak area and carbon peak area for the one or more compounds from the hydrocarbon sample; and scaling the hydrogen to carbon peak area ratio to calculate a hydrogen to carbon ratio for the one or more compounds.

In still another embodiment, a method is provided for characterizing the ratio of hydrogen to carbon in a sample. The method includes separating a plurality of compounds in a first hydrocarbon sample using gas chromatography; measuring atomic emissions from carbon atoms and hydrogen atoms for one or more compounds from the first hydrocarbon sample, the measured atomic emissions corresponding to a first carbon peak area and a first hydrogen peak area; separating a plurality of compounds in a second hydrocarbon sample using gas chromatography; measuring atomic emissions from carbon atoms and hydrogen atoms for one or more compounds from the second hydrocarbon sample, the measured atomic emissions corresponding to a second carbon peak area and a second hydrogen peak area; calculating a normalizing factor for the first carbon peak area, the first carbon peak area multiplied by the normalizing factor corresponding to the second carbon peak area; normalizing the first hydrogen peak area based on the normalizing factor; and comparing the normalized first hydrogen peak area and the second hydrogen peak area.

DETAILED DESCRIPTION OF THE EMBODIMENTS

Overview

Figure 1:
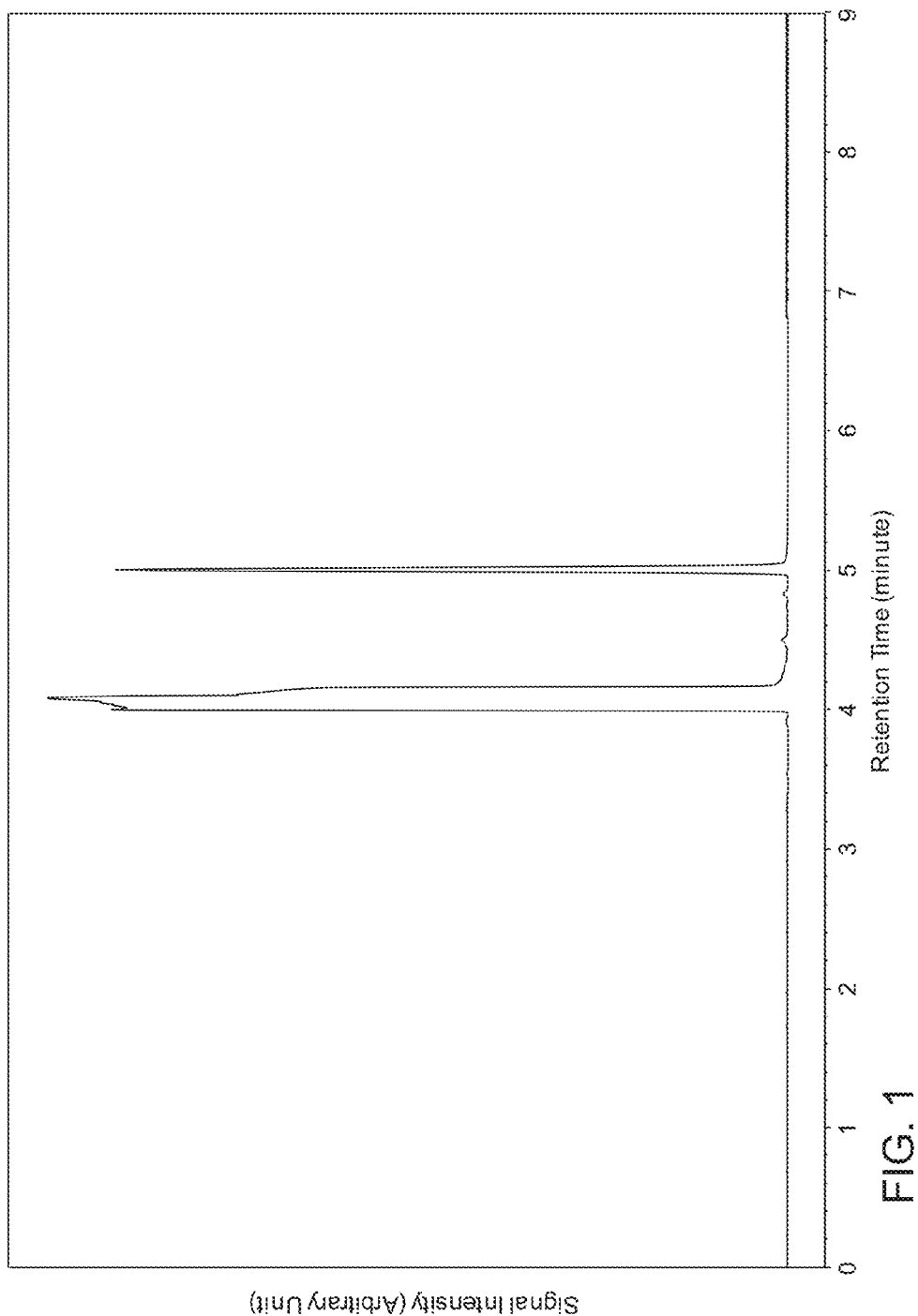
FIGS. 1 to 4 show chromatograms generated according to the invention for various compounds.

In various embodiments, methods are provided for determining the relative carbon to hydrogen ratio of a hydrocarbon mixture, or alternatively of one or more compounds within a hydrocarbon mixture, in comparison with another hydrocarbon sample. The determination is performed by using an atomic emission detector to measure an emission peak for both carbon and hydrogen in a sample. The atomic emission detector is fed by passing the sample through a chromatograph, such as a gas chromatograph, so that separate peaks are obtained for the one or more compounds within a sample. The relative carbon to hydrogen ratio for the sample and/or for compounds within the sample is then determined by comparing the area under the carbon peak with the area under the hydrogen peak for a given compound. This can be repeated for up to all of the compounds within the sample.

By using the ratio of hydrogen peak are to carbon peak area, in some embodiments the relative carbon to hydrogen ratio of two samples can be compared without further normalization. In particular, a relative comparison of carbon to hydrogen ratio in two samples can be performed without having to develop an extensive sample library of compounds that are known via characterization by other techniques. This can allow for direct comparison of refinery feedstocks and/or product streams without requiring separate measurements performed on a reference stream.

In some optional embodiments, the methods can further allow for an approximately quantitative determination of carbon to hydrogen ratio of a hydrocarbon mixture, or alternatively of one or more compounds within a hydrocarbon mixture. If the atomic emission detector is used to determine carbon to hydrogen ratio for one or more compounds with known amounts of carbon and hydrogen, a scaling factor can be determined When the ratio of hydrogen peak area to carbon peak area is determined for an unknown compound, this scaling factor can then be used to provide a value for the compound. By using the ratio of hydrogen peak area to carbon peak area, it is noted that the scaling factor can be determined based on analysis of a relative small number of known reference samples.

The carbon to hydrogen ratio for a hydrocarbon compound in a petroleum feed is related to its value as a fuel for heating or for other energy related applications. For example, a fuel for use in an internal combustion engine or in a heating system is typically burned or combusted with oxygen via chemical reactions that generate heat and combustion products such as carbon dioxide and water. A fuel is usually a group or mixture of primarily hydrocarbon compounds. The abundance of hydrogen atoms in the fuel has a direct impact on the heating value or energy that can be generated during the burning. Measuring the carbon and hydrogen abundances in a fuel, as well as the carbon to hydrogen ratio in the fuel, would allow for evaluation and/or estimation of the energy value that will be released upon combustion of the fuel. More generally, characterizing the carbon to hydrogen ratio of a hydrocarbon sample, or of compounds within a sample, can provide an indication of the energy content and/or overall value of the sample.

For many petroleum and/or biologically derived feed streams, including feed or product streams within a refinery, the chemical composition is not completely known. Measuring the carbon to hydrogen ratio of a hydrocarbon stream is one way to determine the energy related application value of a stream with an at least partially unknown composition. The carbon to hydrogen ratio can also be used to determine the possibility of further refining of a feed or product stream to produce lower boiling temperature fractions for use in fuel or heating applications.

Conventional techniques are available that can measure both carbon and hydrogen intensities in a hydrocarbon sample. Examples include nuclear magnetic resonance (NMR) testing or the combustion method for carbon, hydrogen, and nitrogen elemental analysis. However, both of these techniques are bulk phase measurement techniques that determine values for an overall sample. Such conventional methods do not provide for separation of the sample prior to or during analysis, such as chromatographic type separation of the sample.

In various embodiments, gas chromatography (GC) and/or comprehensive two dimensional gas chromatography (GC× GC) is used in association with an atomic emission detector (AED) to measure the carbon and hydrogen abundance of a sample. The AED, as a GC detector, can detect carbon and hydrogen intensity of each component detected by turning into atomic emission lines correlated to atomic emissions for both carbon and hydrogen. Preferably, the atomic emission lines selected for carbon and hydrogen are grouped closely enough together that the same emission detector can be used to detect both signals. For example, carbon has an atomic emission at 496 nm, while hydrogen has an atomic emission at 486 nm. These emissions are grouped sufficiently close together so that both emissions can be measured at the same time using a single detector.

In this description, reference will be made to hydrocarbon streams or hydrocarbon mixtures. Hydrocarbon streams or mixtures are defined herein to include streams or mixtures containing heteroatoms. As understood by those of skill in the art, typical mineral oil or biologically derived feedstocks often include compounds containing heteroatoms, such as (but not limited to) compounds containing sulfur, nitrogen, and/or oxygen. For a biologically derived feedstock, such heteroatoms may correspond to 10-15% by weight or more of the raw feed before processing. Unless it is specifically indicated otherwise, hydrocarbon streams or hydrocarbon mixtures are defined to include streams or mixtures containing such heteroatoms. This includes streams or mixtures from both mineral oil sources and from biologically derived sources.

Feedstocks

A mineral feedstock refers to a petroleum feedstock derived from crude oil that has optionally been subjected to one or more separation and/or other refining processes. As noted above, a mineral oil feedstock may be referred to as a hydrocarbon feedstock, but it is understood that heteroatoms other than carbon and hydrogen may also be present in such a mineral feedstock. The mineral feedstock can be a petroleum feedstock boiling in the naphtha range or above, but more typically the feedstock will boil in the diesel range or above. Heavy oil feeds can also be characterized using the methods described herein. Examples of suitable feeds can include atmospheric gas oils, vacuum gas oils, light cycle oils, and/or other heavy oil feeds. The final boiling point of a feed can be up to about 1200° F. Other examples of suitable feedstocks can include, but are not limited to, virgin distillates, hydrotreated virgin distillates, kerosene, diesel boiling range feeds (such as hydrotreated diesel boiling range distillates, hydroprocessed diesel boiling range distillates, or fluid catalytic cracking diesel boiling range distillates), and the like, and combinations thereof.

In an embodiment, a feedstock can have an initial boiling point of at least about 400° F. (204° C.), or at least about 450° F. (232° C.), or at least about 500° F. (260° C.), or at least about 550° F. (288° C.), or at least about 600° F. (316° C.), or at least about 650° F. (343° C.). In another embodiment, the feedstock can have a final boiling point of about 1200° F. (649° C.) or less, or about 1100° F. (593° C.) or less, or about 1050° F. (566° C.) or less, or about 1000° F. (538° C.) or less, or about 900° F. (482° C.) or less. Alternatively, the feedstock can be characterized by the boiling point required to boil a specified percentage of the feed. For example, the temperature required to boil at least 5 wt % of a feed is referred to as a "T5" boiling point. Preferably, the feedstock has a T5 boiling point at least about 400° F. (204° C.), or at least about 450° F. (232° C.), or at least about 500° F. (260° C.), or at least about 550° F. (288° C.), or at least about 600° F. (316° C.), or at least about 650° F. (343° C.), or at least about 665° F. (352° C.). Preferably, the feedstock has a T95 boiling point of about 1150° F. (621° C.) or less, or about 1100° F. (593° C.) or less, or about 1050° F. (566° C.) or less, or about 1000° F. (538° C.) or less, or about 900° F. (482° C.) or less, or about 850° F. (454° C.) or less. Examples of suitable feeds include various atmospheric and/or vacuum gas oil feeds, diesel boiling range feeds, and feeds corresponding to mixtures thereof.

The sulfur and nitrogen content of the sample may be any convenient value. The measurement of the carbon peak area and hydrogen peak area for a compound is not directly dependent on the presence of other heteroatoms, such as sulfur, nitrogen, or oxygen. The carbon to hydrogen ratio determinations described herein may be performed prior to and/or after hydrotreatment of a sample to remove heteroatom impurities.

Determination of carbon to hydrogen ratio may also be performed on samples that include at least a portion of a biologically derived oil, such as a biocomponent feedstock. In the discussion below, a biocomponent feedstock refers to an oil derived from a biological raw material component, from biocomponent sources such as vegetable, animal, fish, and/or algae. In this discussion, a reference to a biologically derived oil or biocomponent oil is understood to include biologically derived oils, fats, or other compounds suitable for use in place of or as a supplement to a mineral oil. Note that, for the purposes of this document, vegetable fats/oils refer generally to any plant based material, and can include fat/oils derived from a source such as plants of the genus *Jatropha*. Generally, the biocomponent sources can include vegetable fats/oils, animal fats/oils, fish oils, pyrolysis oils, and algae lipids/oils, as well as components of such materials, and in some embodiments can specifically include one or more type of lipid compounds. Lipid compounds are typically biological compounds that are insoluble in water, but soluble in nonpolar (or fat) solvents. Non-limiting examples of such solvents include alcohols, ethers, chloroform, alkyl acetates, benzene, and combinations thereof.

Major classes of lipids include, but are not necessarily limited to, fatty acids, glycerol-derived lipids (including fats, oils and phospholipids), sphingosine-derived lipids (including ceramides, cerebrosides, gangliosides, and sphingomyelins), steroids and their derivatives, terpenes and their derivatives, fat-soluble vitamins, certain aromatic compounds, and long-chain alcohols and waxes.

In living organisms, lipids generally serve as the basis for cell membranes and as a form of fuel storage. Lipids can also be found conjugated with proteins or carbohydrates, such as in the form of lipoproteins and lipopolysaccharides.

Examples of vegetable oils that can be used in accordance with this invention include, but are not limited to rapeseed (canola) oil, soybean oil, coconut oil, sunflower oil, palm oil, palm kernel oil, peanut oil, linseed oil, tall oil, corn oil, castor oil, *jatropha* oil, jojoba oil, olive oil, flaxseed oil, camelina oil, safflower oil, babassu oil, tallow oil, and rice bran oil.

Vegetable oils as referred to herein can also include processed vegetable oil material. Non-limiting examples of processed vegetable oil material include fatty acids and fatty acid alkyl esters. Alkyl esters typically include $C_1$-$C_5$ alkyl esters. One or more of methyl, ethyl, and propyl esters are preferred.

Examples of animal fats that can be used in accordance with the invention include, but are not limited to, beef fat (tallow), hog fat (lard), turkey fat, fish fat/oil, and chicken fat. The animal fats can be obtained from any suitable source including restaurants and meat production facilities.

Animal fats as referred to herein also include processed animal fat material. Non-limiting examples of processed animal fat material include fatty acids and fatty acid alkyl esters. Alkyl esters typically include $C_1$-$C_5$ alkyl esters. One or more of methyl, ethyl, and propyl esters are preferred.

Algae oils or lipids are typically contained in algae in the form of membrane components, storage products, and metabolites. Certain algal strains, particularly microalgae such as diatoms and cyanobacteria, contain proportionally high levels of lipids. Algal sources for the algae oils can contain varying amounts, e.g., from 2 wt % to 40 wt % of lipids, based on total weight of the biomass itself.

Algal sources for algae oils include, but are not limited to, unicellular and multicellular algae. Examples of such algae include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui,* and *Chlamydomonas reinhardtii*.

The biocomponent feeds usable in the present invention can include any of those which comprise primarily triglycerides and free fatty acids (FFAs). The triglycerides and FFAs typically contain aliphatic hydrocarbon chains in their structure having from 8 to 36 carbons, preferably from 10 to 26 carbons, for example from 14 to 22 carbons. Types of triglycerides can be determined according to their fatty acid constituents. The fatty acid constituents can be readily determined using Gas Chromatography (GC) analysis. This analysis involves extracting the fat or oil, saponifying (hydrolyzing) the fat or oil, preparing an alkyl (e.g., methyl) ester of the saponified fat or oil, and determining the type of (methyl) ester using GC analysis. In one embodiment, a majority (i.e., greater than 50%) of the triglyceride present in the lipid material can be comprised of $C_{10}$ to $C_{26}$, for example $C_{12}$ to $C_{18}$, fatty acid constituents, based on total triglyceride present in the lipid material. Further, a triglyceride is a molecule having a structure substantially identical to the reaction product of glycerol and three fatty acids. Thus, although a triglyceride is described herein as being comprised of fatty acids, it should be understood that the fatty acid component does not necessarily contain a carboxylic acid hydrogen. Other types of feed that are derived from biological raw material components can include fatty acid esters, such as fatty acid alkyl esters (e.g., FAME and/or FAEE).

Gas Chromatograph and Atomic Emission Detector

In various embodiments, the carbon to hydrogen ratio of a sample, either as a relative value or a quantitative value, is determined using gas chromatography to perform a separation on a sample followed by using an atomic emission detector to measure peaks for carbon and hydrogen. For the gas chromatography, any convenient type of gas chromatography equipment may be used. Examples of suitable types of gas chromatography include gas chromatography (GC), high resolution gas chromatography (HRGC), and comprehensive two-dimensional gas chromatograph (GC×GC).

One example of a suitable gas chromatography system and atomic emission detector suitable is an Agilent 6890 gas chromatograph (Agilent Technology Inc., Wilmington, Del.). The Agilent 6890 is suitable for use in performing HRGC. The system is configured with a split/splitless inlet, a capillary column, and an atomic emission detection system. The column is a BPX-5, 30 m, 0.25 mm i.d., 1.0 μm film (SGE Inc., Austin, Tex.). The output from the gas chromatograph is used to feed an atomic emission detector (AED) from Joined Analytics System Inc. The AED setup and the analysis conditions followed the recommendations from the manufacturer's specifications. The carbon emission line (496 nm) and the hydrogen emission line (486 nm) were chosen for the HRGC experiments described herein. The data sampling rate was 2 Hz.

In an example of a measurement performed using such an HRGC and AED apparatus, a 1.0 μL sample was injected at 300° C., with a 250:1 split. The carrier gas was helium in the constant flow mode at 2.0 mL/min. The oven temperature was ramped from 150° C., with 10° C./min increment, to 240° C. The total run time was 9 min. Chemstation (from Agilent Technology Inc.) was used for data acquisition and qualitative analysis was performed by integrating peak area in the Chemistation application.

For comprehensive two-dimensional gas chromatography (GC×GC), a suitable system is an Agilent 6890 gas chromatograph (Agilent Technology, Wilmington, Del.) configured with a split/splitless inlet, capillary columns, and detector. The capillary column system contains a first-dimensional column, which is a BPX-5, 30 m, 0.25 mm i.d., 1.0 μm film, and a second-dimensional column, which is a BPX-50, 2 m, 0.25 mm i.d., 0.25 μm film. Both columns are manufactured by SGE Inc. (Austin, Tex.). There is a looped jet thermal modulation assembly (Zoex Corp., Lincoln, Nebr.) located in between the first and the second dimension columns. This modulator assembly contains a liquid nitrogen cooled "trap-release" jet thermal modulator with a looped transfer column. The detection system contains an atomic emission detector (AED) (Joined Analytics System Inc.) The AED setup and the analysis conditions followed the recommendations from the manufacturer's specifications. The carbon emission line (496 nm) and the hydrogen emission line (486 nm) were chosen for the experiments described herein. The data sampling rate was 10 Hz.

In an example of a measurement performed using such a GC×GC and AED apparatus, a 1.0 μL of a commercial diesel sample was injected at 300° C. at a 250:1 split ratio. The carrier gas was helium in the constant flow mode at 2.0 mL/min. The oven temperature was ramped from 60° C., at 3.0° C./min increment, to 300° C. The modulation period was 10 s. Data acquisition was completed using Chemstation (from Agilent Technology Inc.). Acquired data were processed further for qualitative and quantitative analysis. For qualitative analysis, the data were converted to a two-dimensional image that was processed by a program called "Transform" (Research Systems Inc., Boulder, Colo.). The two-dimensional image was further treated by "PhotoShop" program (Adobe System Inc., San Jose, Calif.) to generate publication ready images.

Example of Compound Comparisons and Method for Establishing a Scaling Factor

As an initial example of determining carbon to hydrogen ratio for compounds based on comparing hydrogen peak areas and carbon peak areas, a series of hydrocarbons containing 10 carbons was studied. Hydrocarbons containing 10 carbon atoms were selected as a matter of convenience, since all of the compounds were a liquid at room temperature but still had reasonably low boiling points. For this study of compounds containing 10 carbon atoms, the hydrocarbons were placed in a toluene solution. The toluene solvent provided a convenient comparison compound for each measurement to demonstrate the ability of the apparatus to distinguish between compounds while allowing for detection of atomic emissions. Table 1 provides a listing of the hydrocarbon compounds that were investigated.

TABLE 1

| Formula | Name | C # | H # | Ratio of area under peak H/C |
|---|---|---|---|---|
| $C_{10}H_6$ | 1,3-Diethyl Benzene | 10 | 6 | 1.14 |
| $C_{10}H_8$ | Naphthalene | 10 | 8 | 1.53 |
| $C_{10}H_{10}$ | 1,2-dihydronaphthalene | 10 | 10 | 1.97 |
| $C_{10}H_{12}$ | Tetraline | 10 | 12 | 2.41 |
| $C_{10}H_{14}$ | Butylbenzene | 10 | 14 | 2.84 |
| $C_{10}H_{16}$ | Terpinene | 10 | 16 | 3.29 |
| $C_{10}H_{18}$ | Decaline | 10 | 18 | 3.68 |
| $C_{10}H_{20}$ | 1-Decene | 10 | 20 | 4.08 |
| $C_{10}H_{20}$ | n-Butyl-Cyclohexane | 10 | 20 | 4.08 |
| $C_{10}H_{20}$ | t-Butyl-Cyclohexane | 10 | 20 | 4.09 |
| $C_{10}H_{22}$ | Decane | 10 | 22 | 4.54 |

As shown in Table 1, the 11 sample compounds included 10 carbons and various amounts of hydrogen. The compounds included both aromatic and non-aromatic compounds.

Figure 2:
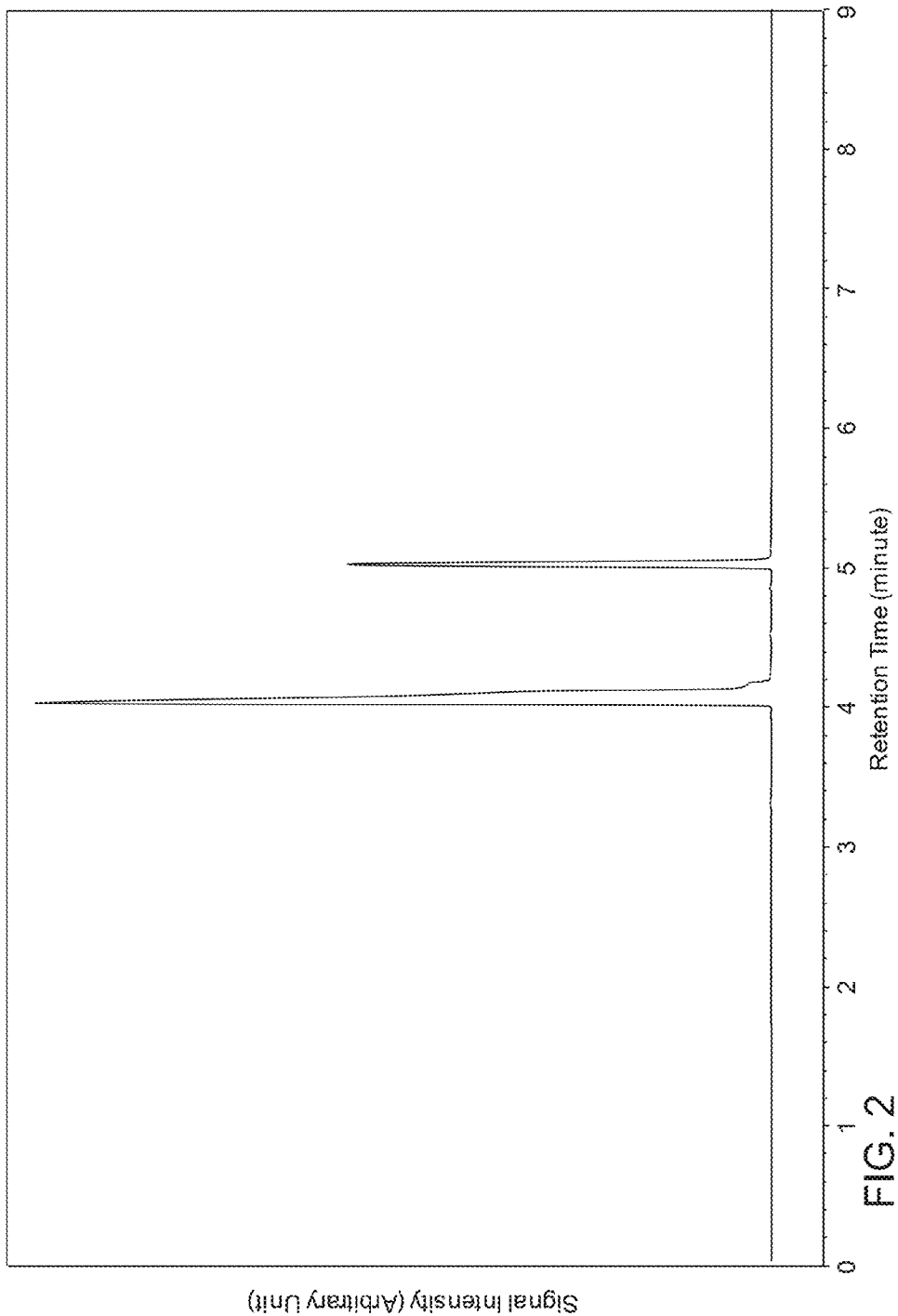

In order to generate a consistent, repeatable ratio of the peak areas for carbon and hydrogen, each of the compounds containing 10 carbon atoms was solvated in toluene at a concentration of 1 mole of compound per liter of toluene. The toluene solution of the compound was then injected into a detection apparatus corresponding to the HRGC and AED detection apparatus described above. Atomic emissions were detected for each sample at 496 nm (carbon) and 486 nm (hydrogen). FIGS. 1 and 2 show examples, respectively, of a carbon emission chromatogram and a hydrogen emission chromatogram for decane, $C_{10}H_{24}$. In FIGS. 1 and 2, the chromatograms contain a larger peak at about 4 minutes of retention time and a smaller peak at about 5 minutes of retention time. The larger peaks correspond to the toluene carrier solvent. The smaller peaks in each chromatogram at about 5 minutes of retention time correspond to the emission due to decane. Thus, FIGS. 1 and 2 demonstrate a first feature of the method, as the peaks for toluene and decane are clearly separated in the chromatograms. Since the carrier compound can be distinguished from the sample compound of interest, the carrier compound can be excluded from any carbon to hydrogen ratio determinations made for a desired compound. It is noted that in some embodiments, a carrier or solvent containing a heteroatom may be used. Although such a carrier or solvent is not strictly a hydrocarbon, a sample using such a carrier or solvent may still be referred to as a hydrocarbon sample unless specifically noted otherwise.

Based on FIGS. 1 and 2, the ratio of the peak areas for carbon and hydrogen for decane can be determined. The peak area for carbon can be determined based on the chromatogram in FIG. 1, while the peak area for hydrogen can be determined based on the chromatogram in FIG. 2. Such a peak area determination can be performed, for example, by any of a variety of commercially available programs for analyzing chromatograms or other spectroscopic data.

Figure 3:
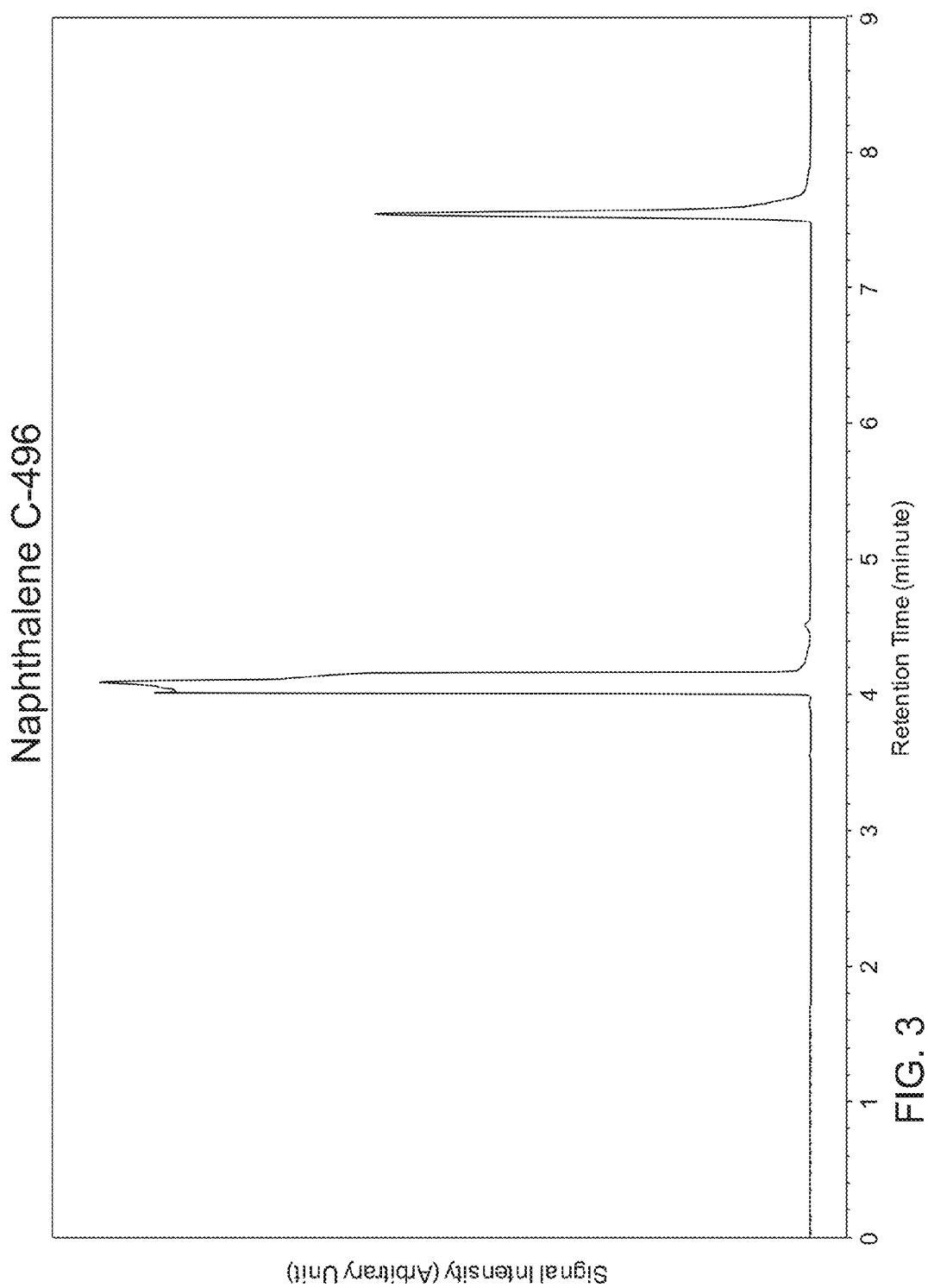
Figure 4:
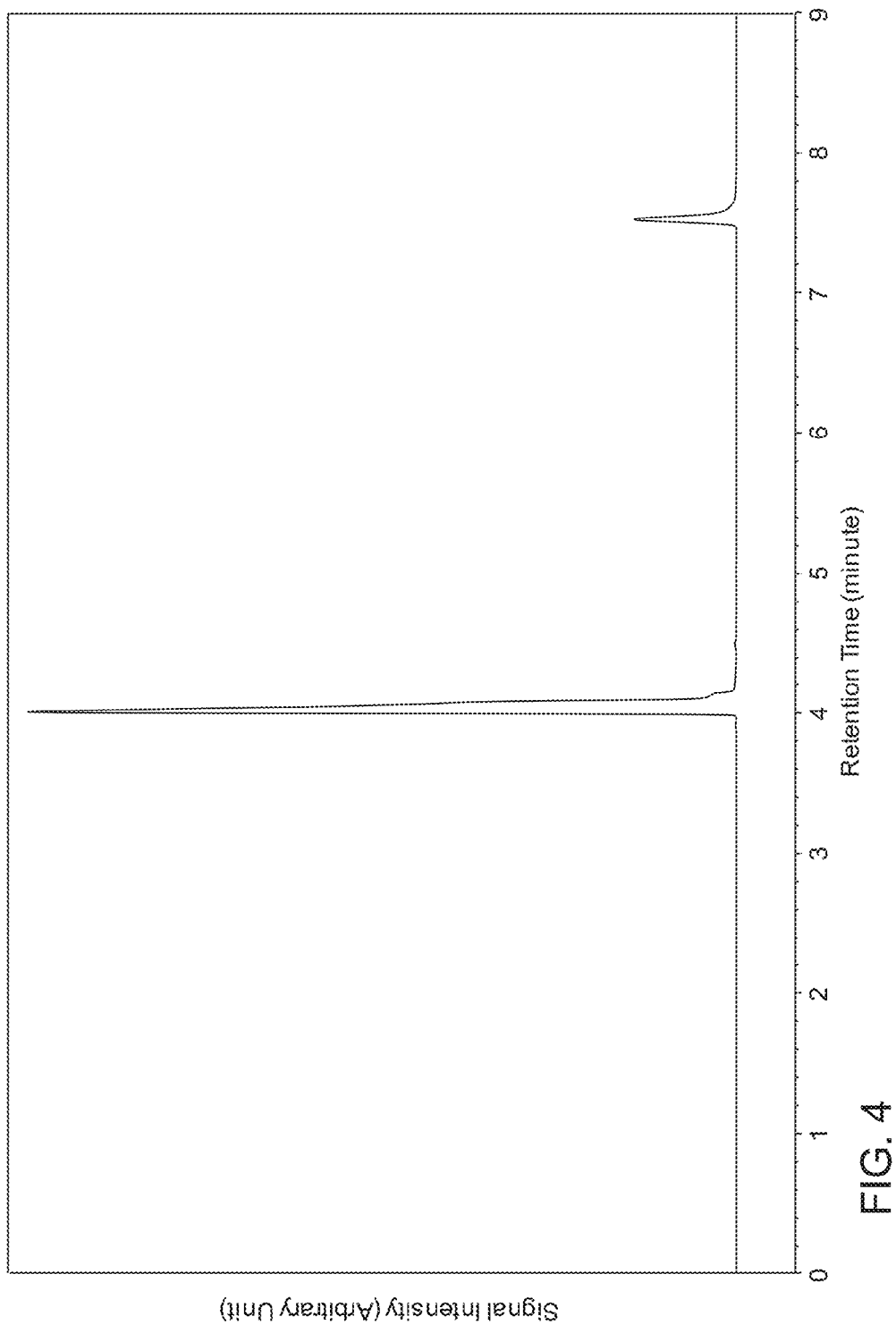

FIGS. 3 and 4 show, respectively, carbon and hydrogen chromatograms for naphthalene, $C_{10}H_8$. Once again, the peak at about 4 minutes corresponds to the toluene solvent while the peak near 7.6 minutes corresponds to the naphthalene. The ratio of hydrogen peak area to carbon peak area can also be calculated for naphthalene. The ratio of hydrogen peak area to carbon peak area for naphthalene is 1.53, as shown in Table 1, while the ration of hydrogen peak area to carbon peak area for decane is 4.54. A comparison of the peak area ratios provides a qualitative determination that the hydrogen to carbon ratio in decane is larger than the hydrogen to carbon ratio in naphthalene. Based on this comparison, it is expected that decane will provide a higher energy content than naphthalene when used as a fuel or in other applications where a compound is combusted. This comparison demonstrates another feature of the invention, as this comparison was made without having to perform a regression analysis or another type of calculation to determine a scaling factor. More generally, this type of technique can be used to compare the hydrogen to carbon ratio for two mixtures of compounds, such as two different heavy oil samples, to provide a qualitative estimate of the energy content of the samples. Alternatively, such a comparison could compare the suitability of such heavy oil samples for further refining based on the relative hydrogen to carbon content of the samples. Still another option is to determine a hydrogen to carbon peak area ratio for a desired compound or mixture of compounds for use as a reference. Evaluations of how to further process an unknown feedstock can be made based on a comparison of the hydrogen to carbon peak area ratio of the unknown feedstock with the reference compound or mixture of compounds.

Figure 5:
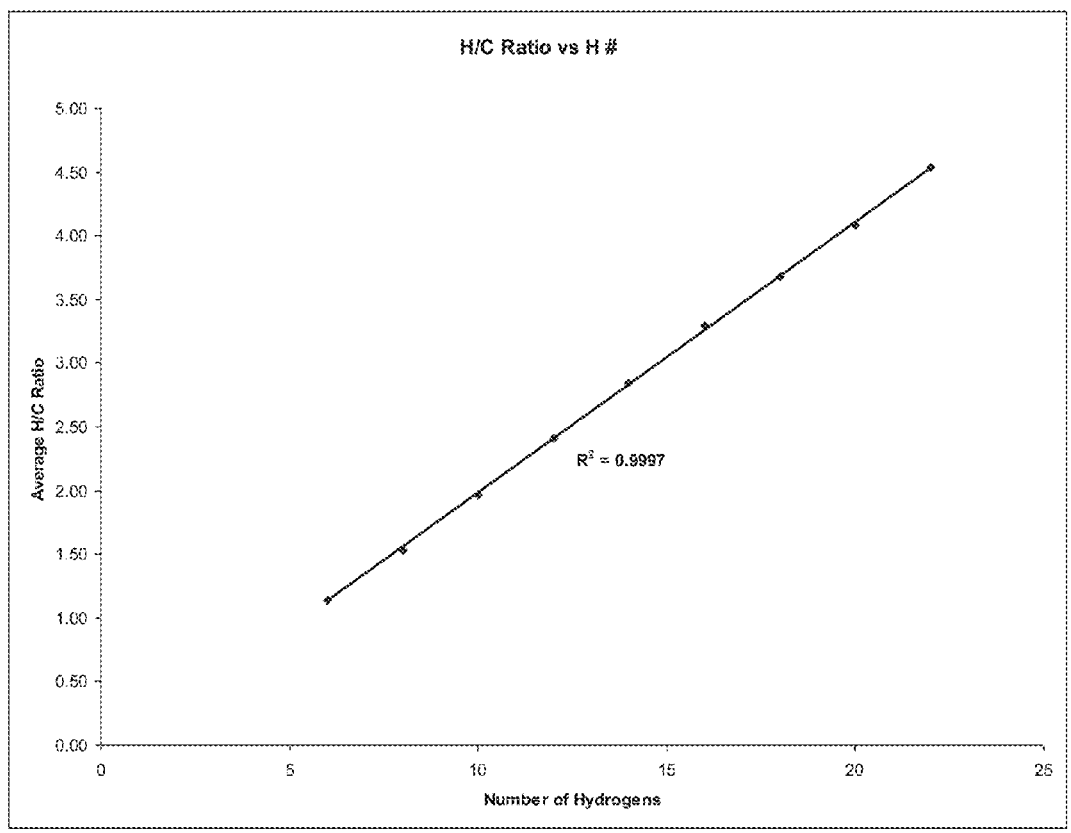
FIG. 5 shows a comparison of the ratio of hydrogen peak area to carbon peak area for a series of sample compounds relative to the hydrogen content of the sample compounds.

The chromatograms shown in FIGS. 1 to 4 demonstrate the capability of a GC plus AED method to determine relative hydrogen to carbon content values for various samples. As shown in Table 1, additional chromatograms were generated for the rest of the compounds containing 10 carbon atoms. The hydrogen to carbon area ratio values shown in Table 1 are plotted relative to the number of hydrogens in each compound in FIG. 5. FIG. 5 confirms that ratio of hydrogen to carbon areas is correlated with the ratio of hydrogen to carbon in a compound in a predictable manner. This correlation is independent of the variations between aromatic and non-aromatic compounds in the compounds. The series of values shown in Table 1 and plotted in FIG. 5 can be used to calculate a scaling factor for converting a measured ratio of hydrogen to carbon peak area to a ratio of hydrogens to carbons in a corresponding sample. Based on the correlation shown in FIG. 5, the correlation appears to be that the ratio of hydrogen to carbon peak areas from atomic emission detection is about a factor of two greater than the ratio of hydrogens to carbons in a sample.

Examples of GC/AED on a Heavy Oil and Diesel Samples

The above description demonstrated the capabilities of a gas chromatography and atomic emission detection method for comparing individual compounds. In various embodiments, the systems and methods described herein can also be used to characterize samples containing multiple compounds, such as a fuel sample, a heavy oil sample, or a sample of a stream in a refinery.

Figure 6:
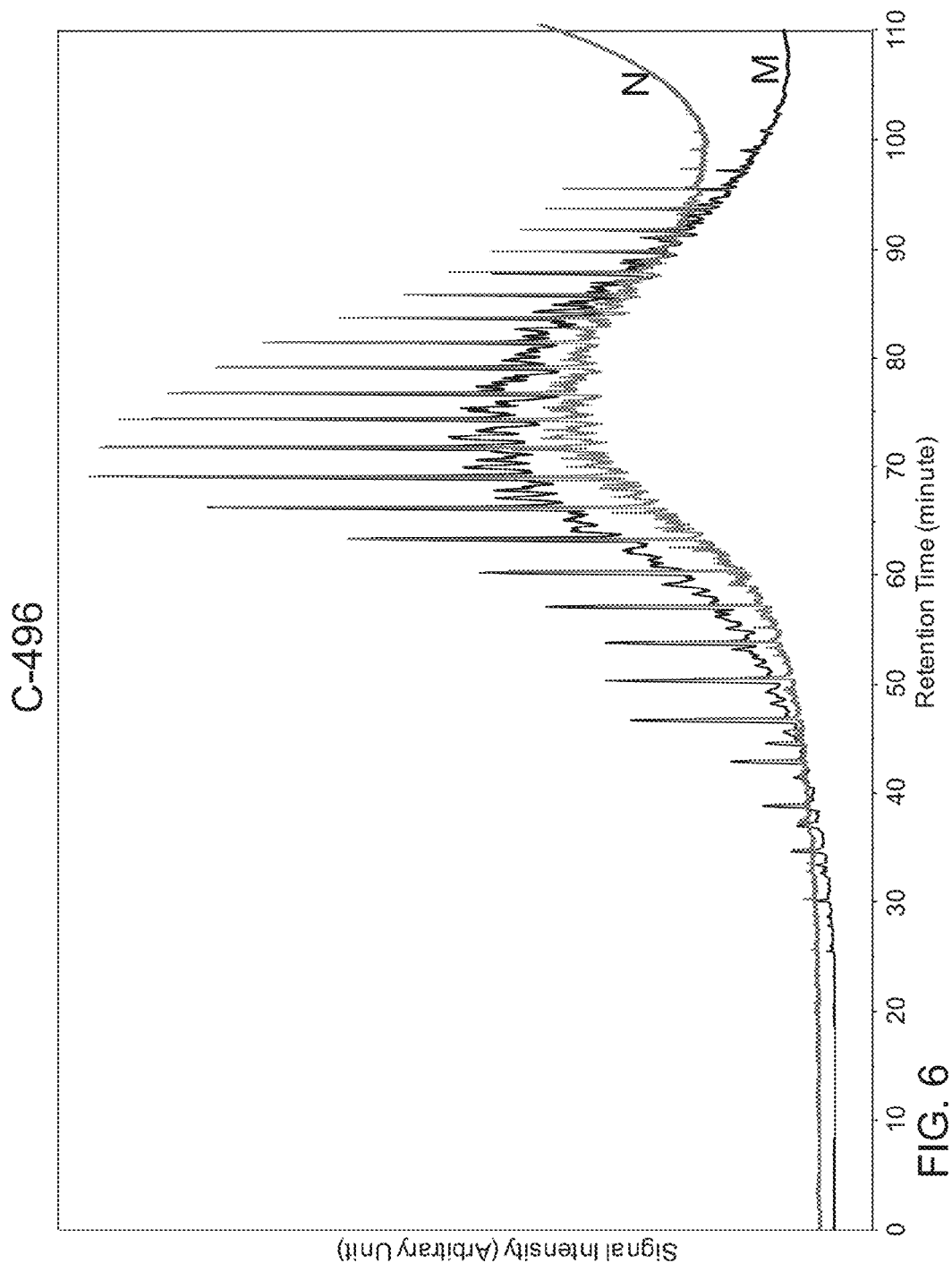
FIGS. 6 and 7 show chromatograms generated according to the invention for heavy oil samples.
Figure 7:
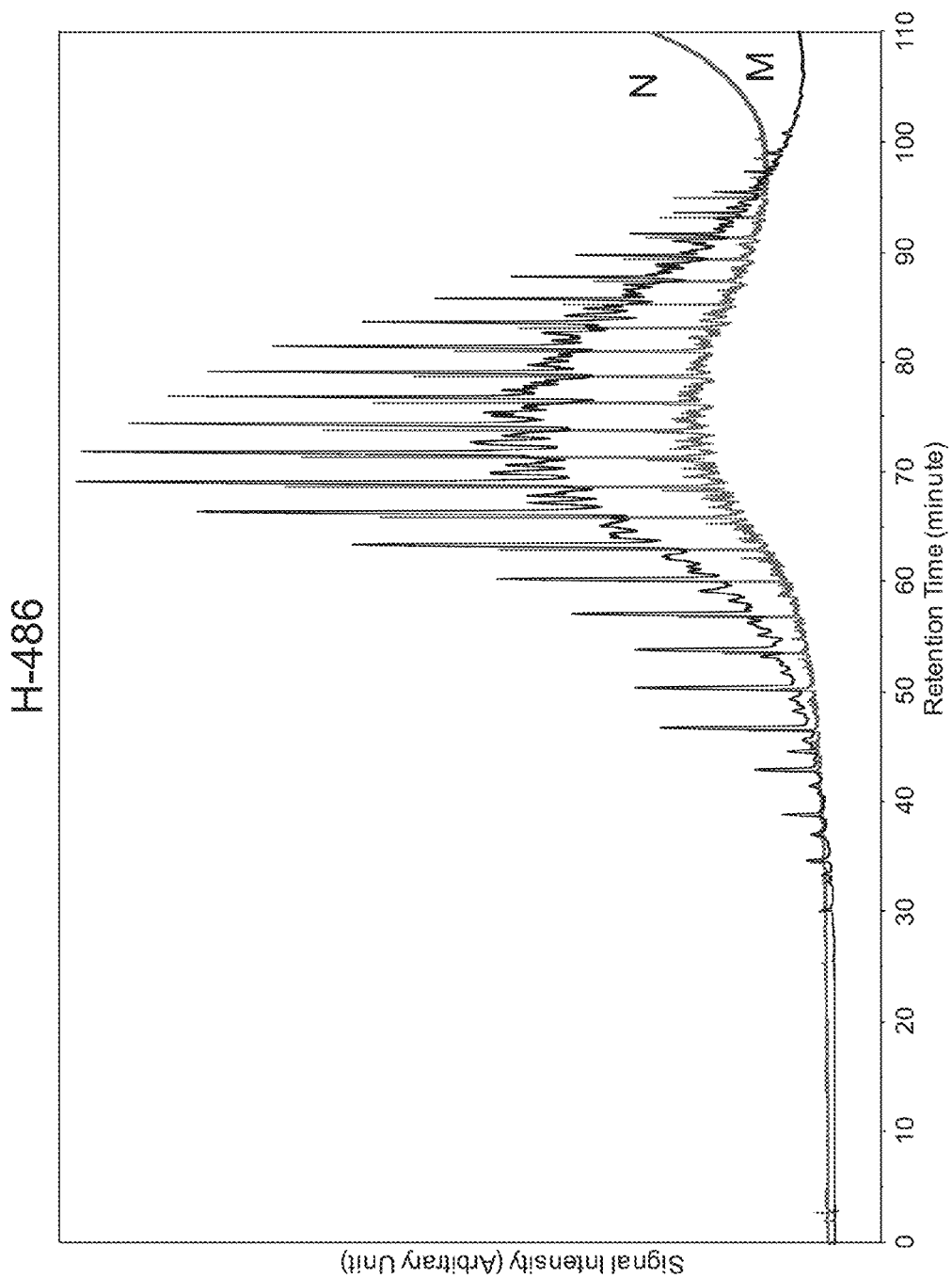

FIG. 6 shows examples of chromatograms at 486 nm (carbon) for two heavy oil samples. The chromatograms were generated using an HRGC and AED apparatus as described above. The HRGC conditions were similar to the conditions used for the model compound study. For the heavy oil samples, the oven temperature was ramped from 60° C. to 390° C. by raising the temperature 3° C. per minute. The upper chromatogram in FIG. 6, labeled "M," corresponds to a heavy oil sample containing primarily saturated molecules. The lower chromatogram, labeled "N," corresponds to a heavy oil sample containing approximately equal amounts of saturated and aromatic compounds. The chromatogram labeled "M" crosses over the chromatogram labeled "N" at about 95 minutes of retention time, resulting in the tail of the "M" chromatogram being below the tail of the "N" chromatogram. FIG. 7 similarly shows the hydrogen chromatograms for heavy oils M and N.

As shown in FIGS. 6 and 7, the chromatographs provide a series of discrete peaks, with each peak representing one or more compounds that passes through the chromatography column at roughly the same time. Each of these peaks can be evaluated separately to determine a ratio for a hydrogen peak area versus the carbon peak area. By summing all of the hydrogen peak areas and all of the carbon peak areas, a ratio for the overall heavy oil sample can be determined. By determining this ratio for both heavy oil samples, the heavy oil sample with the higher ratio of hydrogen to carbon can be identified. This can allow, for example, identification of the heavy oil with the lowest hydrogen to carbon ratio. Such a heavy oil can be diverted to a process that handles fractions with reduced hydrogen to carbon ratios, such as coking.

As another example, a hypothetical refinery may have capacity for both fluid catalytic cracking of a feed and coking of heavy oil feeds. Fluid catalytic cracking of a heavy oil feed leads to higher value products such as naphtha and gasoline, but yield will be poor if a feed with a low ratio of hydrogen to carbon is used. Because of the poor yield, fluid catalytic cracking of a feed with a low ratio of hydrogen to carbon will also likely result in excess coke formation, which is typically burned off as $CO_2$ in an FCC process. As an alternative, a feed with a low ratio of hydrogen to carbon may be processed using a coker. Coking typically leads to a larger portion of lower value products, such as heavy heating oils and asphalt. However, the excess carbon in a coker forms a solid coke, as opposed to generating $CO_2$. For a petroleum sample with a low hydrogen to carbon ratio, coking provides a method for increasing the amount of carbon in the sample that is retained in a product as opposed to being lost to $CO_2$.

A GC/AED measurement may be used to determine whether a heavy oil feed is more suitable for fluid catalytic cracking or coking. In an embodiment, a heavy oil feed can be selected for use in fluid catalytic cracking based on the feed having a hydrogen peak area to carbon peak area ratio of at least about 2.4, or at least about 2.6, or at least about 2.8. A feed with a ratio of hydrogen peak area to carbon peak area less than such a threshold value can be used as a coker feed. Alternatively, a hydrogen to carbon ratio derived from the hydrogen peak area and carbon peak area may be used. In such an embodiment, a heavy oil feed can be selected for use in fluid catalytic cracking based on a threshold ratio value of hydrogen to carbon in the feed of at least about 1.2, or at least about 1.3, or at least about 1.4.

The threshold value for determining whether to use a feed for fluid catalytic cracking versus coking will typically depend on a variety of factors, such as the relative availability of feeds for a given refinery and the current demand (or price) for the fuels generated from fluid catalytic cracking. At higher demand levels for gasoline and other distillates, it can be beneficial to perform fluid catalytic cracking on feeds with lower ratios of hydrogen peak area to carbon peak area.

As an alternative to calculating ratios of hydrogen peak area to carbon peak area, the chromatograms for two samples can instead be compared by normalizing the chromatograms. For example, the total peak area can be determined for all of the peaks in the carbon chromatograms for two samples. If the areas are different, the first carbon chromatogram can be multiplied by a factor so that the areas under both carbon chromatograms are the same. The factor used to normalize the first carbon chromatogram can then be used to normalize the first hydrogen chromatogram. The normalized first hydrogen chromatogram can then be compared directly with the second chromatogram to determine which sample has the larger ratio of hydrogen to carbon.

Still another option using the data shown in FIGS. 6 and 7 is to determine the ratio of hydrogen peak area to carbon peak area for individual peaks in the chromatograms. This can allow for determination of how the ratio of hydrogen peak area to carbon peak area varies with respect to the various compound groupings in a sample. More generally, any convenient grouping of peaks can be used to determine the hydrogen peak area to carbon peak area ratio for the grouping of peaks. Since the speed of movement of a compound in gas chromatography is roughly correlated with molecular weight, and single molecular weight roughly correlates with boiling point, this type of analysis can provide some insight as to how the hydrogen to carbon ratio of an unknown sample changes as a function of the boiling point.

Figure 8:
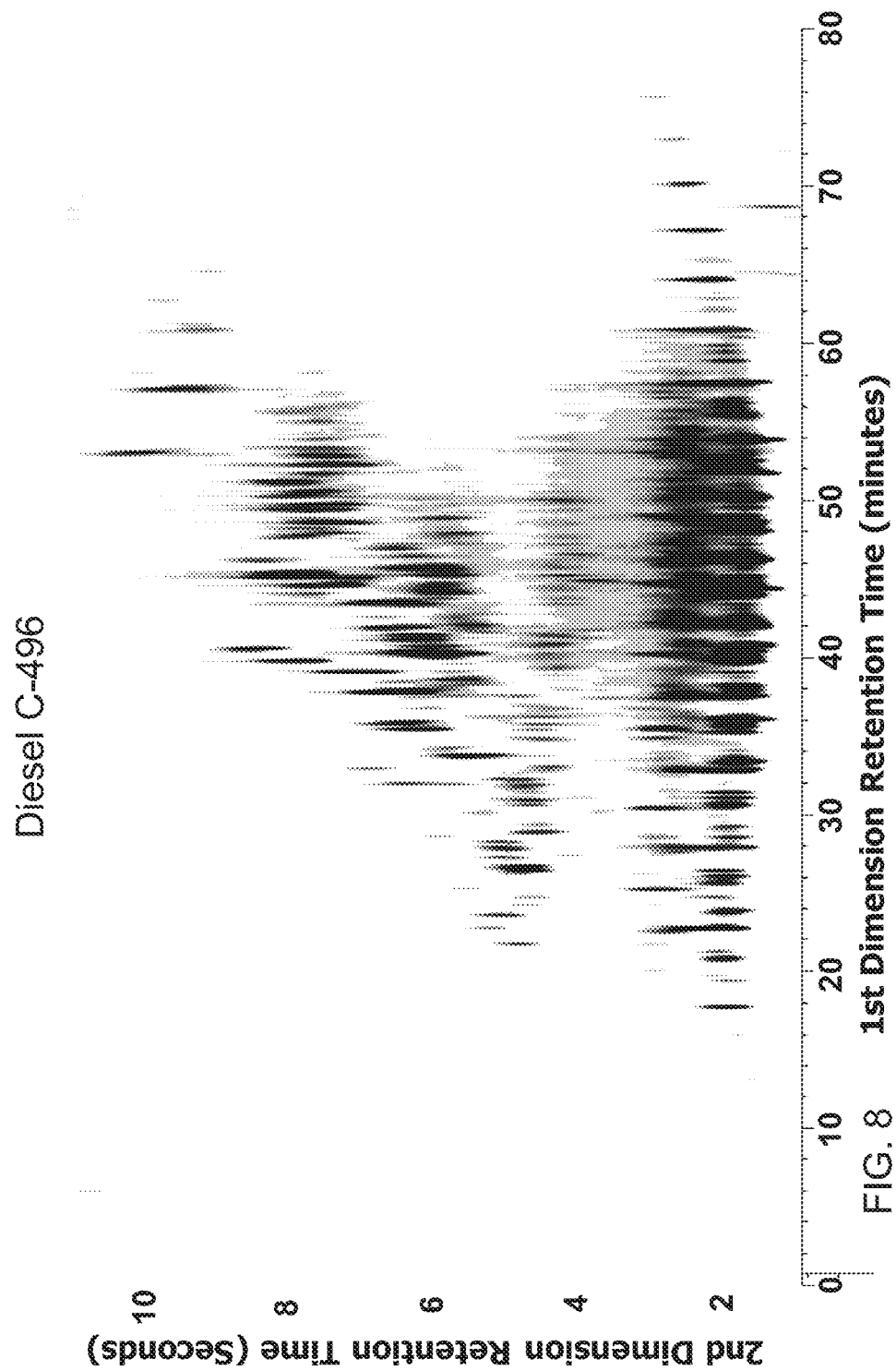
FIGS. 8 and 9 show chromatograms generated according to the invention for diesel fuel samples.
Figure 9:
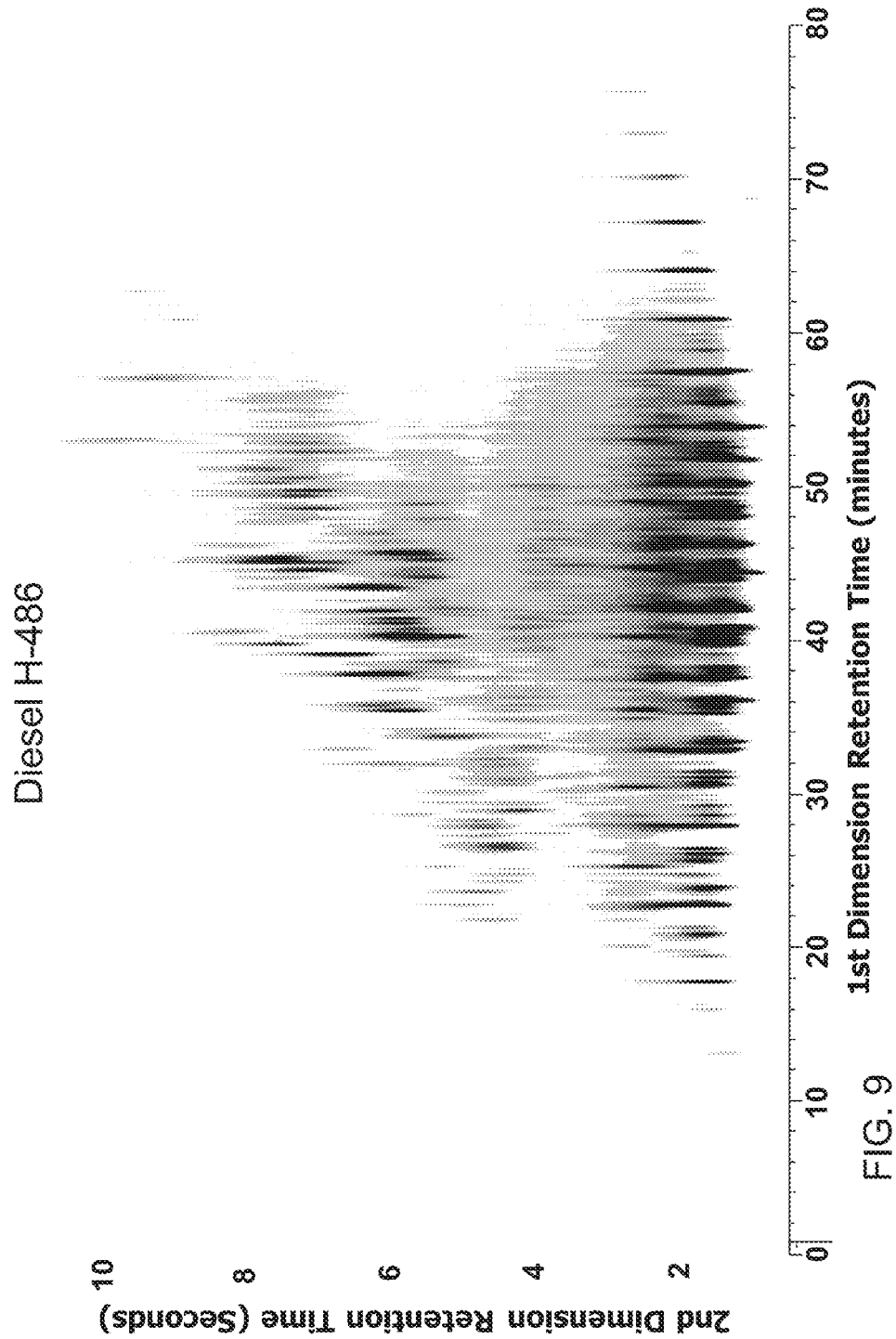

If even greater detail is desired in terms of identifying the hydrogen and carbon contributions of individual compounds, a two dimensional gas chromatography method can be used to feed the atomic emission detector. FIG. 8 shows GC×GC and AED carbon chromatograph for a commercial diesel fuel sample, while FIG. 9 shows the corresponding hydrogen chromatograph for the diesel fuel sample. By using the two-dimensional chromatograph, compounds that otherwise would be grouped together in a one-dimensional chromatograph are distinguished. If desired, this allows the hydrogen to carbon ratio for these compounds to be calculated separately.

The ability to determine hydrogen to carbon ratio for individual compounds within a sample, such as by use of high resolution gas chromatography or comprehensive two-dimensional gas chromatograph with atomic emission detection, allows for greater control in determining how to process petroleum feeds. For example, a GC/AED system can be used to better understand the composition of a diesel fuel sample. The gas chromatography retention time for a compound is roughly correlated with boiling point. In a potential diesel fuel sample, the cetane value of a molecule roughly increases with the number of carbon atoms in the molecule until a plateau is reached somewhere between 16 and 20 carbons, depending on the type of molecule. The cetane value of a molecule also roughly increases with increasing hydrogen to carbon ratio, with highly branched compounds providing an exception. These two trends are sometimes in conflict, as heavier petroleum fractions are also fractions that tend to more aromatic compounds.

Using one-dimensional gas chromatography (such as HRGC) with atomic emission detection can provide a rough indication of how the hydrogen to carbon ratio of a feed changes with respect to boiling point. For a potential diesel boiling range feed prior to hydroprocessing, this can provide some indication of the amount of hydrogen needed for hydroprocessing, as aromatic saturation often represents a substantial portion of the hydrogen consumed during hydroprocessing. After hydroprocessing, the hydrogen to carbon peak area ratio can be useful for adjusting cut points for a diesel fuel. For example, the low boiling portions of a diesel fuel are often also suitable for use as a kerosene fraction. If the low boiling portions of a diesel fuel have a hydrogen to carbon peak area ratio that indicates a larger alkane character, the distillation cut point can be adjusted to increase the amount of kerosene retained in the diesel fuel. If the low boiling portions have hydrogen to carbon peak area ratio that indicates rings or other forms of unsaturation, the cut point can be adjusted to include less of the low boiling fraction to avoid reduction in cetane value. Use of a comprehensive two-dimensional gas chromatography method can provide even more information, as compounds having similar retention times can be better distinguished. This allows greater information about the distribution of hydrogen to carbon peak area ratios for a given retention time, as opposed to generating only an average value at each retention time. In other words, comparisons can be made between portions or samples of a feedstock that have different retention times along at least one dimension in the gas chromatography separation.

Additional Embodiments

In a first embodiment, a method is provided for characterizing the ratio of hydrogen to carbon in a sample. The method includes separating a plurality of compounds in a first hydrocarbon sample using gas chromatography; measuring atomic emissions from carbon atoms and hydrogen atoms for one or more compounds from the first hydrocarbon sample; determining a first hydrogen to carbon peak area ratio based on the hydrogen peak area and carbon peak area for the one or more compounds from the first hydrocarbon sample; separating a plurality of compounds in a second hydrocarbon sample using gas chromatography; measuring atomic emissions from carbon atoms and hydrogen atoms for one or more compounds from the second hydrocarbon sample; determining a second hydrogen to carbon peak area ratio based on the hydrogen peak area and carbon peak area for the one or more compounds from the second hydrocarbon sample; and comparing the first hydrogen to carbon peak area ratio and the second hydrogen to carbon peak area ratio. Optionally, at least one of the first hydrocarbon sample and the second hydrocarbon sample corresponds to a refinery feed or product.

In a second embodiment, a method is provided for characterizing the ratio of hydrogen to carbon in a sample. The method includes separating a plurality of compounds in a first hydrocarbon sample using gas chromatography; measuring atomic emissions from carbon atoms and hydrogen atoms for one or more compounds from the first hydrocarbon sample, the measured atomic emissions corresponding to a first carbon peak area and a first hydrogen peak area; separating a plurality of compounds in a second hydrocarbon sample using gas chromatography; measuring atomic emissions from carbon atoms and hydrogen atoms for one or more compounds from the second hydrocarbon sample, the measured atomic emissions corresponding to a second carbon peak area and a second hydrogen peak area; calculating a normalizing factor for the first carbon peak area, the first carbon peak area multiplied by the normalizing factor corresponding to the second carbon peak area; normalizing the first hydrogen peak area based on the normalizing factor; and comparing the normalized first hydrogen peak area and the second hydrogen peak area. Optionally, at least one of the first hydrocarbon sample and the second hydrocarbon sample corresponds to a refinery feed or product.

In a third embodiment, a method according to any of the above embodiments is provided, wherein the second hydrocarbon sample comprises a reference compound or a reference mixture of compounds.

In a fourth embodiment, a method according to any of the above embodiments is provided, wherein the first hydrocarbon sample and the second hydrocarbon sample correspond to different feedstocks, or wherein the first hydrocarbon sample and the second hydrocarbon sample correspond to a single feedstock, the first hydrocarbon sample and second hydrocarbon sample having different retention times along at least one dimension in the gas chromatography separation.

In a fifth embodiment, a method according to any of the above embodiments is provided, further comprising selecting at least one distillation cut point for a feedstock corresponding to the first sample based on the comparing of the first hydrogen to carbon peak ratio and the second hydrogen to carbon peak ratio.

In a sixth embodiment, a method according to any of the above embodiments is provided, wherein at least one of the first hydrocarbon sample and the second hydrocarbon sample corresponds to a refinery feed or product.

In a seventh embodiment, a method is provided for characterizing the ratio of hydrogen to carbon in a sample. The method includes separating a plurality of compounds in a first hydrocarbon sample using gas chromatography; measuring atomic emissions from carbon atoms and hydrogen atoms for one or more compounds from the first hydrocarbon sample; determining a hydrogen to carbon peak area ratio based on the hydrogen peak area and carbon peak area for the one or more compounds from the first hydrocarbon sample; and scaling the hydrogen to carbon peak area ratio to calculate a hydrogen to carbon ratio for the one or more compounds.

In an eighth embodiment, a method according to the seventh embodiment is provided, wherein scaling the hydrogen to carbon peak ratio comprises measuring atomic emissions from carbon atoms and hydrogen atoms for a plurality of reference compounds; determining a scaling factor based on hydrogen to carbon peak area ratios for the plurality of reference compounds; and scaling the hydrogen to carbon peak area ratio for the one or more compounds using the determined scaling factor.

In a ninth embodiment, a method is provided according to any of the above embodiments, wherein the first hydrocarbon sample comprises a carrier or solvent. Optionally, the one or more compounds from the first hydrocarbon sample exclude the carrier or solvent.

In a tenth embodiment, a method is provided according to any of the above embodiments, wherein the carbon atomic emissions are measured at 496 nm and the hydrogen atomic emissions are measured at 486 nm.

In an eleventh embodiment, a method is provided according to any of the above claims, wherein the one or more compounds from the first hydrocarbon sample comprise all of the compounds from the first sample.

What is claimed is:

1. A method for characterizing the ratio of hydrogen to carbon in a sample, comprising:
   separating a plurality of compounds in a first hydrocarbon sample using gas chromatography;
   measuring atomic emissions from carbon atoms and hydrogen atoms for one or more compounds from the first hydrocarbon sample;
   determining a first hydrogen to carbon peak area ratio based on the hydrogen peak area and carbon peak area for the one or more compounds from the first hydrocarbon sample;
   separating a plurality of compounds in a second hydrocarbon sample using gas chromatography;
   measuring atomic emissions from carbon atoms and hydrogen atoms for one or more compounds from the second hydrocarbon sample;
   determining a second hydrogen to carbon peak area ratio based on the hydrogen peak area and carbon peak area for the one or more compounds from the second hydrocarbon sample; and
   comparing the first hydrogen to carbon peak area ratio and the second hydrogen to carbon peak area ratio.

2. The method of claim 1, wherein separating a plurality of compounds results in at least one grouping of two or more compounds that leaves the gas chromatography apparatus during a common retention time period.

3. The method of claim 1 wherein the second hydrocarbon sample comprises a reference compound or a reference mixture of compounds.

4. The method of claim 1, wherein the first hydrocarbon sample comprises a carrier or solvent.

5. The method of claim 4, wherein the one or more compounds from the first hydrocarbon sample exclude the carrier or solvent.

6. The method of claim 1, wherein the carbon atomic emissions are measured at 496 nm and the hydrogen atomic emissions are measured at 486 nm.

7. The method of claim 1, wherein the one or more compounds from the first hydrocarbon sample comprise all of the compounds from the first sample.

8. The method of claim 1, wherein the first hydrocarbon sample and the second hydrocarbon sample correspond to different feedstocks.

9. The method of claim 1, wherein the first hydrocarbon sample and the second hydrocarbon sample correspond to a single feedstock, the first hydrocarbon sample and second hydrocarbon sample having different retention times along at least one dimension in the gas chromatography separation.

10. The method of claim 1, further comprising selecting at least one distillation cut point for a feedstock corresponding to the first sample based on the comparing of the first hydrogen to carbon peak ratio and the second hydrogen to carbon peak ratio.

11. The method of claim 1, wherein at least one of the first hydrocarbon sample and the second hydrocarbon sample corresponds to a refinery feed or product stream.

12. A method for characterizing the ratio of hydrogen to carbon in sample, comprising:
   separating a plurality of compounds in a hydrocarbon sample using gas chromatography;
   measuring atomic emissions from carbon atoms and hydrogen atoms for one or more compounds from the hydrocarbon sample;
   determining a hydrogen to carbon peak area ratio based on the hydrogen peak area and carbon peak area for the one or more compounds from the hydrocarbon sample; and
   scaling the hydrogen to carbon peak area ratio to calculate a hydrogen to carbon ratio for the one or more compounds.

13. The method of claim 12, wherein scaling the hydrogen to carbon peak ratio comprises:
   measuring atomic emissions from carbon atoms and hydrogen atoms for a plurality of reference compounds;
   determining a scaling factor based on hydrogen to carbon peak area ratios for the plurality of reference compounds; and
   scaling the hydrogen to carbon peak area ratio for the one or more compounds using the determined scaling factor.

14. The method of claim 12, wherein the hydrocarbon sample comprises a carrier or solvent.

15. The method of claim 14, wherein the one or r more compounds from the hydrocarbon sample exclude the carrier or solvent.

16. The method of claim 12, wherein the hydrocarbon sample corresponds to a refinery feed or product stream.

17. A method for characterizing the ratio of hydrogen to carbon in a sample, comprising:
   separating a plurality of compounds in a first hydrocarbon sample using gas chromatography;
   measuring atomic emissions from carbon atoms and hydrogen atoms for one or more compounds from the first hydrocarbon sample, the measured atomic emissions corresponding to a first carbon peak area and a first hydrogen peak area;
   separating a plurality of compounds in a second hydrocarbon sample using gas chromatography;
   measuring atomic emissions from carbon atoms and hydrogen atoms for one or more compounds from the second hydrocarbon sample, the measured atomic emissions corresponding to a second carbon peak area and a second hydrogen peak area;
   calculating a normalizing factor for the first carbon peak area, the first carbon peak area multiplied by the normalizing factor corresponding to the second carbon peak area;
   normalizing the first hydrogen peak area based on the normalizing factor; and
   comparing the normalized first hydrogen peak area and the second hydrogen peak area.

18. The method of claim 17, wherein the second hydrocarbon sample comprises a reference compound or a reference mixture of compounds.

19. The method of claim 17, wherein the first hydrocarbon sample comprises a carrier or solvent.

20. The method of claim 19, wherein the one or more compounds from the first hydrocarbon sample exclude the carrier or solvent.

\* \* \* \* \*